United States Patent
Li et al.

(10) Patent No.: US 10,123,686 B2
(45) Date of Patent: Nov. 13, 2018

(54) DROWSINESS DETECTION METHOD AND SYSTEM FOR DETERMINING THE DEGREE OF EYE OPENING AND CLOSURE

(71) Applicant: Wistron Corporation, New Taipei (TW)

(72) Inventors: Chong-Wei Li, New Taipei (TW); Chih-Pin Liao, New Taipei (TW); Che-You Kuo, New Taipei (TW)

(73) Assignee: Wistron Corporation, New Taipei (TW)

( * ) Notice: Subject to any disclaimer, the term of this patent is extended or adjusted under 35 U.S.C. 154(b) by 255 days.

(21) Appl. No.: 14/923,451

(22) Filed: Oct. 27, 2015

(65) Prior Publication Data
US 2016/0310060 A1 Oct. 27, 2016

(30) Foreign Application Priority Data

Apr. 22, 2015 (TW) ............................ 104112946 A

(51) Int. Cl.
*G06K 9/00* (2006.01)
*A61B 3/00* (2006.01)
(Continued)

(52) U.S. Cl.
CPC ............ *A61B 3/0025* (2013.01); *A61B 3/10* (2013.01); *A61B 3/113* (2013.01); *A61B 3/14* (2013.01); *A61B 5/1103* (2013.01); *A61B 5/18* (2013.01); *A61B 5/4809* (2013.01); *A61B 5/7485* (2013.01); *A61B 3/0008* (2013.01);
(Continued)

(58) Field of Classification Search
None
See application file for complete search history.

(56) References Cited

U.S. PATENT DOCUMENTS 5,805,745 A * 9/1998 Graf .................. G06K 9/00268
348/14.07
5,878,156 A * 3/1999 Okumura ........... G06K 9/00268
340/575

(Continued)

OTHER PUBLICATIONS

W. Burger and M. J. Burge. Chapter 2, Regions in Binary Images. "Principles of Digital Image Processing—Core Algorithms (vol. 2)". Undergraduate Topics in Computer Science. Springer, London (2009).*

(Continued)

*Primary Examiner* — Vu Le
*Assistant Examiner* — Samah A Beg
(74) *Attorney, Agent, or Firm* — Winston Hsu

(57) ABSTRACT

An eye detection method for detecting a degree of eye opening and closure of a testee includes detecting a location of an eye pupil, a location of an inner eye corner and a location of an outer eye corner of an eye of the testee; calculating an eye width according to the location of the inner eye corner and the location of the outer eye corner; multiplying the eye width by a specific ratio to obtain an eye height; generating a region of interest with a center on the location of the eye pupil, a length equal to the eye width, and a width equal to the eye height; and determining a ratio of the eye occupying a detection area in the region of interest, and determining the degree of eye opening and closure of the testee accordingly.

17 Claims, 16 Drawing Sheets

(51) Int. Cl.
*A61B 5/11* (2006.01)
*A61B 3/113* (2006.01)
*A61B 3/14* (2006.01)
*A61B 3/10* (2006.01)
*A61B 5/00* (2006.01)
*A61B 5/18* (2006.01)

(52) U.S. Cl.
CPC ........... *A61B 5/1128* (2013.01); *A61B 5/6893* (2013.01); *A61B 5/7203* (2013.01); *A61B 5/7405* (2013.01); *A61B 2503/22* (2013.01); *A61B 2576/00* (2013.01); *G06K 9/0061* (2013.01)

(56) References Cited

U.S. PATENT DOCUMENTS

| | | | | |
|---|---|---|---|---|
| 6,571,002 | B1* | 5/2003 | Ogawa | G06F 17/153 340/575 |
| 2002/0081032 | A1* | 6/2002 | Chen | G06K 9/00228 382/199 |
| 2004/0090334 | A1* | 5/2004 | Zhang | B60K 28/066 340/575 |
| 2007/0154096 | A1* | 7/2007 | Cao | G06K 9/00234 382/190 |
| 2008/0101659 | A1* | 5/2008 | Hammoud | G08B 21/06 382/118 |
| 2008/0317385 | A1* | 12/2008 | Nakada | G06K 9/0061 382/305 |
| 2009/0237515 | A1* | 9/2009 | Lee | H04N 5/232 348/207.99 |
| 2011/0043350 | A1* | 2/2011 | Ben David | B60Q 9/00 340/441 |
| 2012/0219189 | A1* | 8/2012 | Wu | A61B 5/1103 382/103 |
| 2012/0269442 | A1* | 10/2012 | Hermant-Santini | G06K 9/0061 382/195 |
| 2013/0176129 | A1* | 7/2013 | Li | A61B 5/18 340/575 |
| 2014/0139655 | A1* | 5/2014 | Mimar | G08B 21/06 348/77 |
| 2014/0147019 | A1* | 5/2014 | Hanita | G06K 9/00604 382/117 |
| 2014/0168400 | A1* | 6/2014 | Chen | H04N 21/4223 348/78 |
| 2015/0282724 | A1* | 10/2015 | McDuff | A61B 5/02427 600/479 |
| 2015/0310261 | A1* | 10/2015 | Lee | G06K 9/00302 382/203 |
| 2016/0106355 | A1* | 4/2016 | Perugupalli | G06K 9/0061 351/210 |

OTHER PUBLICATIONS

Horng, W. B., Chen, C. Y., Chang, Y., & Fan, C. H. (Mar. 2004). Driver fatigue detection based on eye tracking and dynamk, template matching. In Networking, Sensing and Control, 2004 IEEE International Conference on (vol. 1, pp. 7-12). IEEE.*

Du, Y., Ma, P., Su, X., & Zhang, Y. (Dec. 2008). Driver fatigue detection based on eye state analysis. In Proceedings of the 11th Joint Conference on Information Sciences.*

* cited by examiner

DROWSINESS DETECTION METHOD AND SYSTEM FOR DETERMINING THE DEGREE OF EYE OPENING AND CLOSURE

BACKGROUND OF THE INVENTION

1. Field of the Invention

The present invention relates to an eye detection method and system, and more particularly, to an eye detection method and system capable of determining the degree of eye opening and closure.

2. Description of the Prior Art

In a vehicle safety system, detection of a driver's action is an important issue for safety, and determination of whether the driver is sleepy is an important safety indicator. Modern drowsy detection systems determine whether the driver is sleepy according to the degree of eye opening and closure, wherein the determination is performed by finding out the distance between the upper and lower eyelids to calculate the degree of eye opening and closure. However, this method always suffers from positioning difficulty due to eye blinking of the driver. Different eye sizes of different drivers may also result in wrong determination. Thus, there is a need to provide a more effective eye detection method and system to enhance the performance of drowsy detection, in order to enhance the safety of vehicle movement.

SUMMARY OF THE INVENTION

It is therefore an objective of the present invention to provide an eye detection method and system, which is capable of determining the region of interest of the eye via the location of eye corners, and then determining the degree of eye opening and closure according to the above region of interest. In contrast to the locations of eyelids changing when the eye blinks, the locations of eye corners are fixed and are not easily affected by blinking of eyelids. Therefore, a more accurate determination may be realized by using the locations of eye corners to determine the degree of eye opening and closure.

The present invention discloses an eye detection method for detecting a degree of eye opening and closure of a testee. The eye detection method comprises detecting a location of an eye pupil, a location of an inner eye corner and a location of an outer eye corner of an eye of the testee; calculating an eye width according to the location of the inner eye corner and the location of the outer eye corner; multiplying the eye width by a specific ratio to obtain an eye height; generating a region of interest with a center on the location of the eye pupil, a length equal to the eye width, and a width equal to the eye height; and determining a ratio of the eye occupying a detection area in the region of interest, and determining the degree of eye opening and closure of the testee accordingly.

The present invention further discloses an eye detection system for detecting a degree of eye opening and closure of a testee. The eye detection system comprises a photography device and a processor. The photography device is utilized for detecting a location of an eye pupil, a location of an inner eye corner and a location of an outer eye corner of an eye of the testee. The processor, coupled to the photography device, is utilized for performing the following steps: calculating an eye width according to the location of the inner eye corner and the location of the outer eye corner; multiplying the eye width by a specific ratio to obtain an eye height; generating a region of interest with a center on the location of the eye pupil, a length equal to the eye width, and a width equal to the eye height; and determining a ratio of the eye occupying a detection area in the region of interest, and determining the degree of eye opening and closure of the testee accordingly.

The present invention further discloses an eye detection method for detecting a degree of eye opening and closure of a testee. The eye detection method comprises performing an image binarization on an eye image within a region of interest, to generate a binarized image having an eye region and a non-eye region; performing a filling process on the binarized image to eliminate a noise in the eye region determined to be the non-eye region; detecting an area of the eye region within a detection area in the region of interest after the filling process is accomplished; and determining that the eye of the testee is closed when a number of times the ratio of the eye region occupying the detection area smaller than a threshold value is detected in a specific period of time reaches a specific number.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
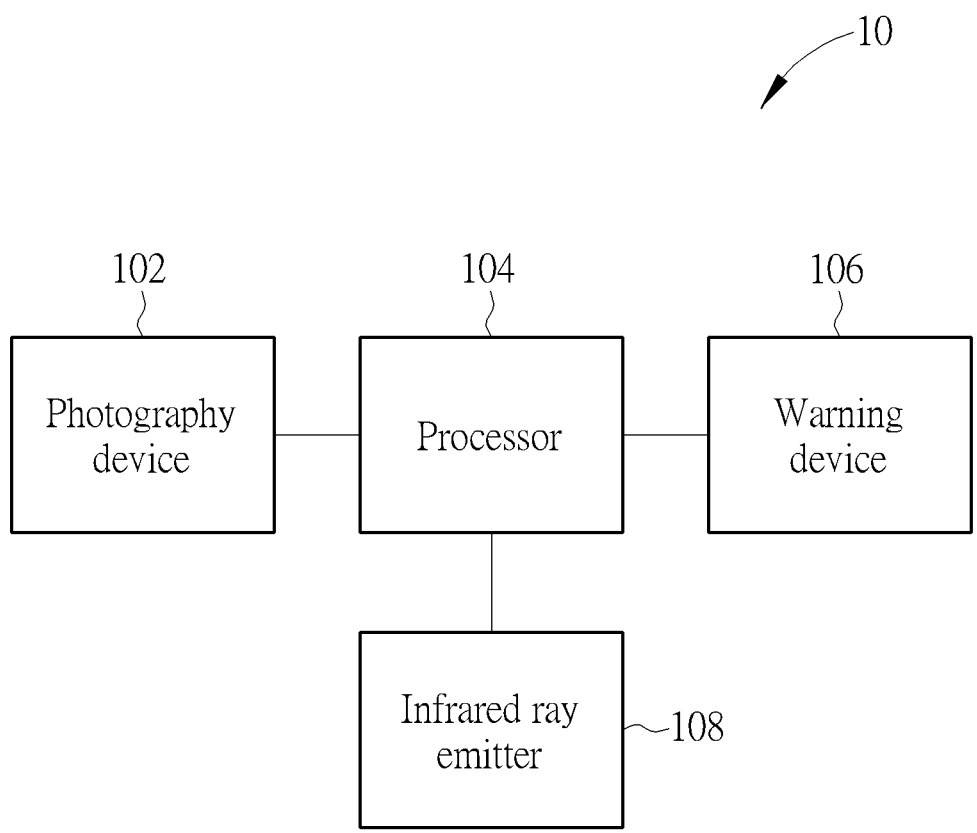
FIG. 1 is a schematic diagram of an eye detection system according to an embodiment of the present invention.

Please refer to FIG. 1, which is a schematic diagram of an eye detection system 10 according to an embodiment of the present invention. The eye detection system 10 is utilized for detecting the degree of eye opening and closure of a testee, e.g., a vehicle driver, in order to determine whether the testee is sleepy. As shown in FIG. 1, the eye detection system 10 includes a photography device 102, a processor 104, a warning device 106 and an infrared ray emitter 108. The photography device 102 is utilized for detecting the location of the eye pupil, the location of the inner eye corner and the location of the outer eye corner. The processor 104, coupled to the photography device 102, is utilized for determining a region of interest corresponding to an eye of the testee according to the locations of the eye pupil, the inner eye corner and the outer eye corner of the eye obtained by the photography device 102. The processor 104 then determines whether the eye is open, narrowed or closed according to the obtained photography image in the region of interest, in order to determine whether the testee is sleepy. The warning device 106, coupled to the processor 104, is utilized for sending a warning signal when the processor 104 determines that the testee is sleepy. The infrared ray emitter 108, coupled to the processor 104, is utilized for performing supplementary illumination on the testee's eye, in order to prevent an image of the eye from being influenced by an external light source. In other words, in several conditions such as the external light is insufficient, the infrared ray emitter 108 may emit infrared light and the photography device 102 may be an infrared light detector, so that the processor 104 may perform following processing according to the infrared image obtained by the photography device 102. On the other hand, in several conditions such as the external light is sufficient, the eye detection system 10 may not turn on the infrared ray emitter 108, or there is no infrared device equipped in the eye detection system 10. In such a condition, the photography device 102 may obtain the eye image by detecting the visible light, and the processor 104 then performs following processing accordingly.

In detail, when the eye detection system 10 detects the degree of eye opening and closure of the testee, the photography device 102 first obtains an image of the eye (or face) of the testee. The photography device 102 may obtain the image by any methods, to obtain the locations of the eye pupil location, the inner eye corner and the outer eye corner of an eye of the testee. In an embodiment, the photography device 102 may obtain the face feature of the testee via the active shape model (ASM) algorithm, in order to retrieve the locations of the eye pupil, the inner eye corner and the outer eye corner from the face feature.

Figure 2:
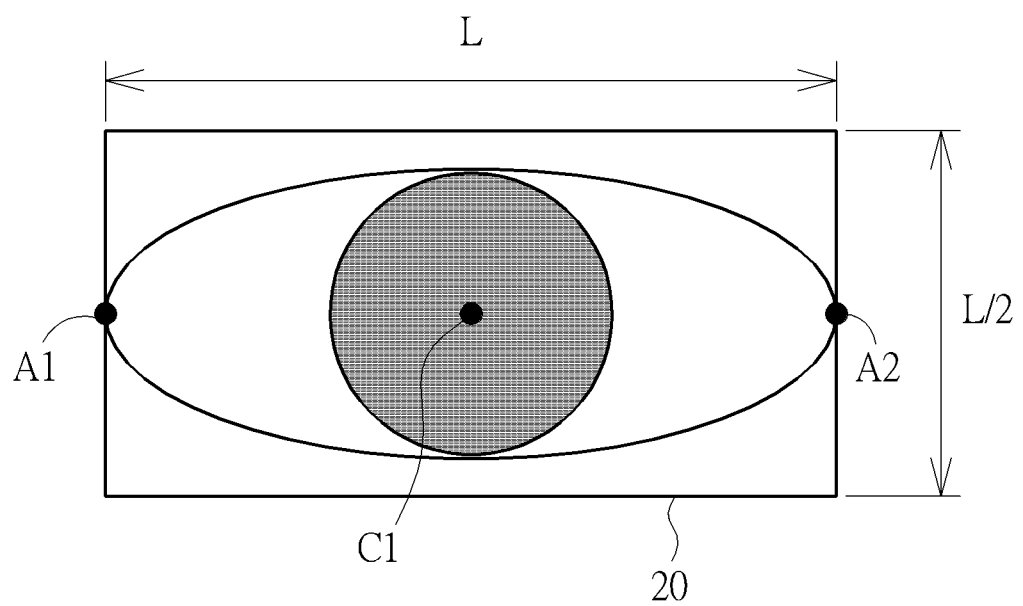
FIG. 2 is a schematic diagram of a region of interest according to an embodiment of the present invention.

Subsequently, the processor 104 may determine a region of interest corresponding to the eye of the testee according to the locations of the eye pupil, the inner eye corner and the outer eye corner obtained by the photography device 102. Please refer to FIG. 2, which is a schematic diagram of a region of interest 20 according to an embodiment of the present invention. As shown in FIG. 2, after the photography device 102 obtains the locations of the inner eye corner A1 and the outer eye corner A2, the processor 104 may calculate an eye width L according to the locations of the inner eye corner A1 and the outer eye corner A2. More specifically, the processor 104 may set the eye width L to be equal to the distance between the inner eye corner A1 and the outer eye corner A2. After determining the eye width L, the processor 104 further sets the eye height. For example, the eye width L may be multiplied by a specific ratio to obtain the eye height. In FIG. 2, the eye width L is multiplied by one second, so that the eye height is equal to L/2. In other embodiments, the specific ratio may be set to different values. For example, the specific ratio may be determined according to the angle of the photography device 102 taking pictures or the eye size of the specific testee, and is not limited herein. After the processor 104 works out the eye width and the eye height, the processor 104 then generates the region of interest 20 corresponding to the eye of the testee, where the center of the region of interest 20 is the location of the eye pupil C1, the length of the region of interest 20 equals the eye width, and the width of the region of interest 20 equals the eye height. As shown in FIG. 2, the region of interest 20 is a rectangular region with a center on the eye pupil, where the length of the rectangular region equals the eye width L and the width of the rectangular region equals the eye height L/2. FIG. 2 illustrates a situation where the image is taken in front of the eye and the eye has a regular shape; hence, the eye image exactly falls within the region of interest 20. In another embodiment, the eye image may not be exactly included in the region of interest due to the angle of the photography device 102 taking pictures or the shape of the eye. In most conditions, however, the region of interest may substantially be regarded as a region where the testee's eye is located. Therefore, the method of determining the degree of eye opening and closure according to the region of interest may achieve a satisfactory determination performance and may not be easily influenced by eye blinking.

Subsequently, the processor 104 may determine a ratio of the eye occupying a detection area in the region of interest 20, and determine the degree of eye opening and closure of the testee accordingly. In detail, the processor 104 first performs image binarization on the image in the region of interest 20 to generate a binarized image including an eye region and a non-eye region. For example, if the image obtained by the photography device 102 is a colored image, the processor 104 may convert a skin color region in the region of interest 20 into black, and convert a non-skin color region in the region of interest 20 into white. If the image obtained by the photography device 102 is a gray scale image, the processor 104 may convert a brighter region into black and convert a darker region into white. Note that the black region maybe regarded as the eye region, and the white region may be regarded as the non-eye region.

Figure 3:
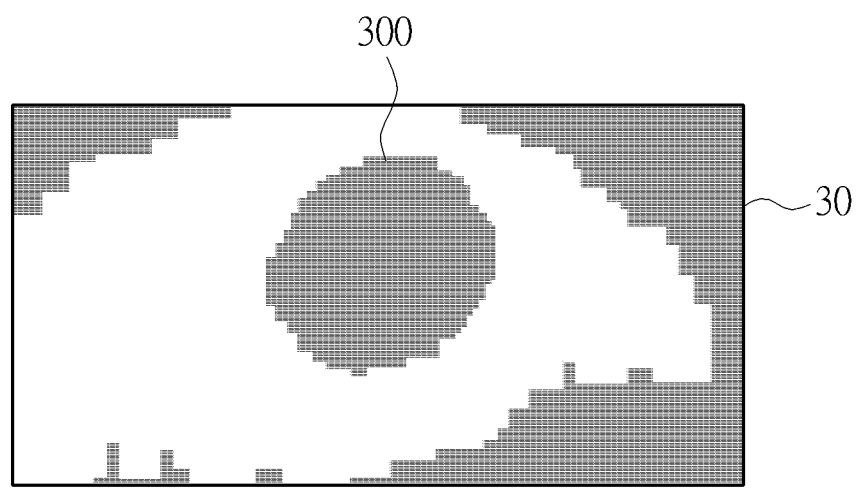
FIG. 3 is a schematic diagram of a binarized image according to an embodiment of the present invention.

However, due to reflection of light or the red-eye phenomenon, the binarized image generated via image binarization may generate a hole at the location of the eye pupil or the center of eyeball; that is, there may exist a noise in the eye region wrongly determined to be the non-eye region. For example, please refer to FIG. 3, which is a schematic diagram of a binarized image 30 according to an embodiment of the present invention. As shown in FIG. 3, the binarized image 30 shows that the red-eye phenomenon causes the eye pupil 300 to be determined to be the non-eye region (i.e., the black area). In such a situation, the location of the eye pupil 300 should be filled to be the eye region (i.e., the white area), to prevent the determination of the degree of eye opening and closure from being affected. The processor 104 may perform a filling process on the binarized image 30 to eliminate the noise in the eye region wrongly determined to be the non-eye region. As a result, the black region on the eye pupil 300 will be filled to be white, so that the white region can accurately correspond to the image of the testee's eye.

Figure 4:
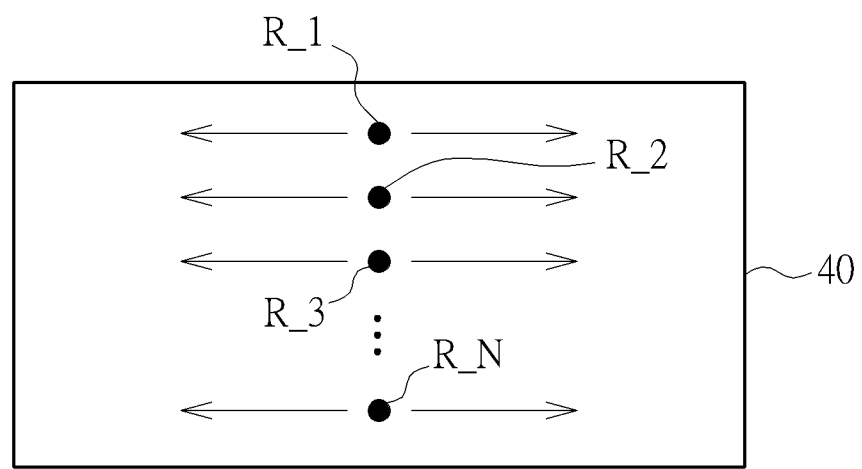
FIG. 4 is a schematic diagram of the filling process performed on the binarized image of a region of interest according to an embodiment of the present invention.

FIG. 4 illustrates detailed operations of the filling process performed on the binarized image of a region of interest 40. As shown in FIG. 4, an implementation method of the filling process is to determine whether the middle point of each row of pixels R_1-R_N in the region of interest 40 is in the eye region or the non-eye region first, and then scan toward the direction of eye width (i.e., the left and right directions, the row direction). If the middle point of a row of pixels is in the non-eye region, the processor 104 may scan leftward and rightward from the middle point. After scanning to the eye region, the processor 104 fills the non-eye region between the middle point of the row of pixels and the scanned eye region to be the eye region. On the other hand, if the middle point of a row of pixels is in the eye region, the processor 104 may scan leftward and rightward from the middle point. After scanning to the non-eye region and then scanning to the eye region, the processor 104 fills the scanned non-eye region in the row of pixels to be the eye region. The operations of the filling process are illustrated by diagrams of the binarized images hereinafter.

Figure 5A:
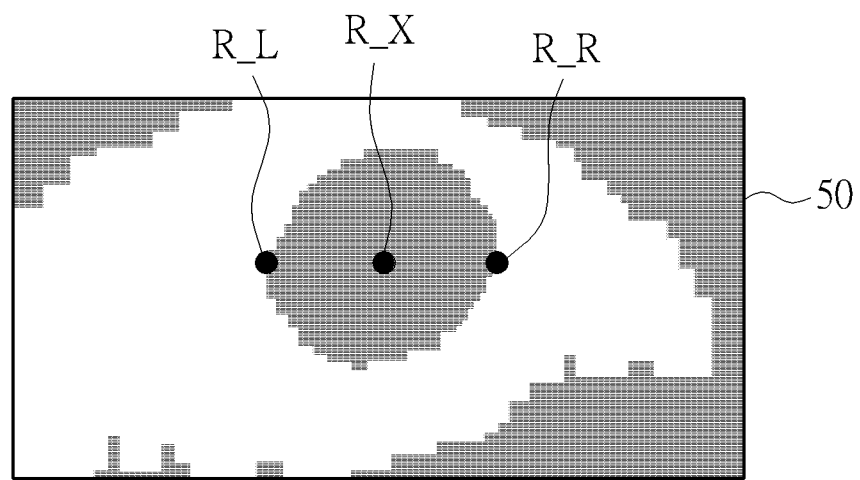
FIG. 5A and FIG. 5B are schematic diagrams of the filling process performed on the binarized image of a region of interest according to an embodiment of the present invention.
Figure 5B:
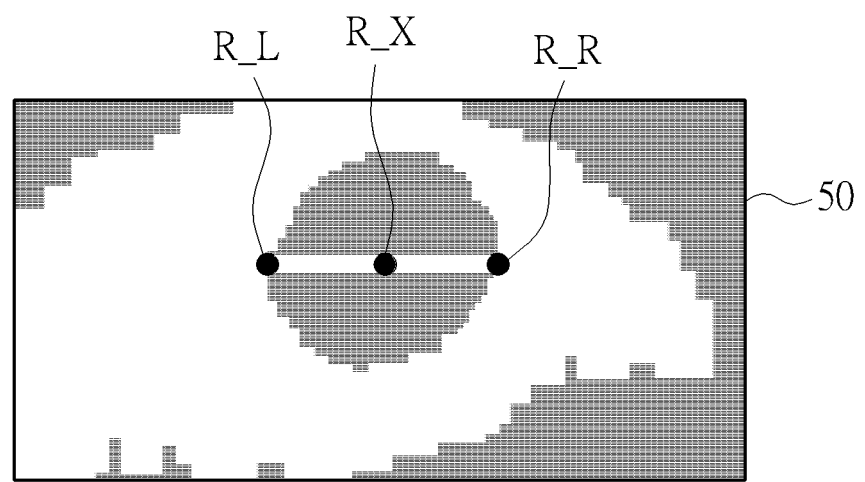

Please refer to FIG. 5A and FIG. 5B, which are schematic diagrams of the filling process performed on the binarized image of a region of interest 50 according to an embodiment of the present invention. As shown in the binarized image of the region of interest 50 in FIG. 5A, the processor 104 may perform the filling process on the $X^{th}$ row of pixels. First of all, the processor 104 finds out the middle point R_X of the $X^{th}$ row of pixels and determines that the middle point R_X is in the non-eye region (i.e., the black region). Subsequently, the processor 104 scans leftward from the middle point R_X. When detecting the eye region (i.e., the white region) at the location of a pixel R_L, the processor 104 may fill the pixel (s) from R_X to R_L in the $X^{th}$ row of pixels to be the eye region. The processor 104 then scans rightward from the middle point R_X. When detecting the eye region at the location of a pixel R_R, the processor 104 may fill the pixel(s) from R_X to R_R in the $X^{th}$ row of pixels to be the eye region. In addition, the pixel corresponding to the middle point R_X may also be filled to be the eye region. The image generated after the $X^{th}$ row of pixels are filled up is illustrated in FIG. 5B.

Figure 6A:
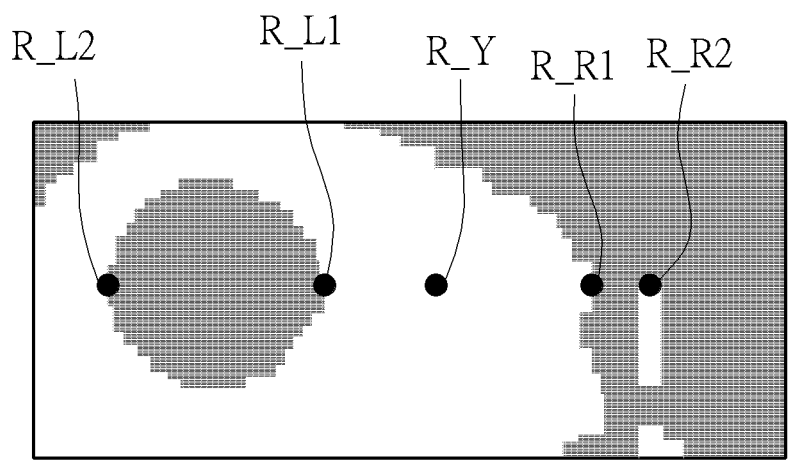
FIG. 6A and FIG. 6B are schematic diagrams of the filling process performed on the binarized image of a region of interest according to an embodiment of the present invention.
Figure 6B:
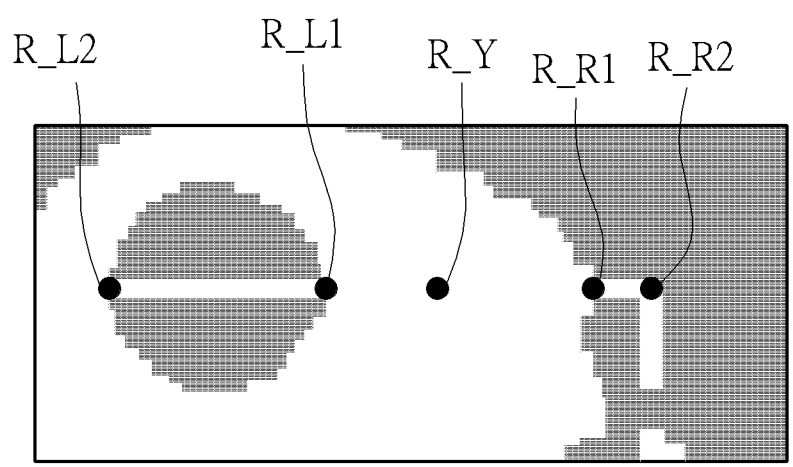

In several conditions, since the locations of noises may be different, the middle point of pixels may be in the eye region. In such a situation, the processor 104 may perform the filling in another manner. For example, please refer to FIG. 6A and FIG. 6B, which are schematic diagrams of the filling process performed on the binarized image of a region of interest 60 according to an embodiment of the present invention. As shown in the binarized image of the region of interest 60 in FIG. 6A, the processor 104 may perform the filling process on the $Y^{th}$ row of pixels. First of all, the processor 104 finds out the middle point R_Y of the $Y^{th}$ row of pixels and determines that the middle point R_Y is in the eye region (i.e., the white region). Subsequently, the processor 104 scans leftward from the middle point R_Y. When detecting the non-eye region (i.e., the black region) at the location of a pixel R_L1, the processor 104 further scans leftward and detects the eye region at the location of a pixel R_L2. The processor 104 thereby fills the pixel(s) from R_L1 to R_L2 in the $Y^{th}$ row of pixels to be the eye region. The processor 104 then scans rightward from the middle point R_Y. When detecting the non-eye region at the location of a pixel R_R1, the processor 104 further scans rightward and detects the eye region at the location of a pixel R_R2. The processor 104 thereby fills the pixel(s) from R_R1 to R_R2 in the $Y^{th}$ row of pixels to be the eye region. The image generated after the $Y^{th}$ row of pixels are filled up is illustrated in FIG. 6B.

By the above methods, the processor 104 may in order perform filling on each row of pixels according to whether the middle point in each row is in the eye region or the non-eye region. As a result, the noise located in the eye region wrongly determined to be the non-eye region, e.g., the noise generated due to light reflection or the red-eye phenomenon, can be eliminated effectively, so that the eye region may accurately correspond to the image of the testee's eye.

Preferably, the processor 104 may perform the filling process on each row of pixels in the region of interest in order. Alternatively, the processor 104 may selectively perform the filling process on partial rows of pixels in the region of interest according to determination requirements of the degree of eye opening and closure and possible statuses of the eye image, in order to increase the efficiency of performing the filling process and also prevent a waste of operating resources of the processor 104.

Please note that the above filling process for each row only needs to perform filling on the first detected non-eye region during the scanning process. This is because the filling process scans from the middle point in each row of pixels toward both sides, and the noises having to be filled are always located in central regions. Further, the detection areas mainly used for determining the degree of eye opening and closure are located in central regions. Therefore, the scanning and filling process only needs to be performed on the first detected non-eye region. After the first detected non-eye regions in the row of pixels on the left-hand side and the right-hand side are both filled up, the processor 104 may perform the filling process on the next row of pixels without scanning further left and right regions.

In several conditions, several noise patterns may not be successfully filled by the above filling processes. For example, when the testee's eye corner is wet, light reflection may also occur in the eye corner region, causing both of the eye corner and eye pupil in the binarized image appear to be black as the non-eye region. In such a situation, the filling effect cannot be achieved with the scan along the horizontal direction, and a scan along the vertical direction is thereby required. For example, please refer to FIG. 7A and FIG. 7B, which are schematic diagrams of the filling process performed on the binarized image of a region of interest 70 according to an embodiment of the present invention. Different from the above binarized image where only the region of eye pupil needs to be filled, in the binarized image of the region of interest 70, the eye pupil and the right eye corner are wrongly determined to be in the non-eye region, such that the above filling process cannot fill the non-eye region on the right-hand side. In such a situation, the processor 104 may further apply the filling process to fill along the vertical direction. In other words, in the region of interest 70, the processor 104 first determines whether the middle point of each column of pixels is in the eye region or the non-eye region, and then scans toward the direction of eye height (i.e., the up and down directions, the column direction). If the middle point of a column of pixels is in the non-eye region, the processor 104 may scan upward and downward from the middle point. After scanning to the eye region, the processor 104 fills the non-eye region between the middle point of the column of pixels and the scanned eye region to be the eye region. On the other hand, if the middle point of a column of pixels is in the eye region, the processor 104 may scan upward and downward from the middle point. After scanning to the non-eye region and then scanning to the eye region, the processor 104 fills the scanned non-eye region in the column of pixels to be the eye region.

Figure 7A:
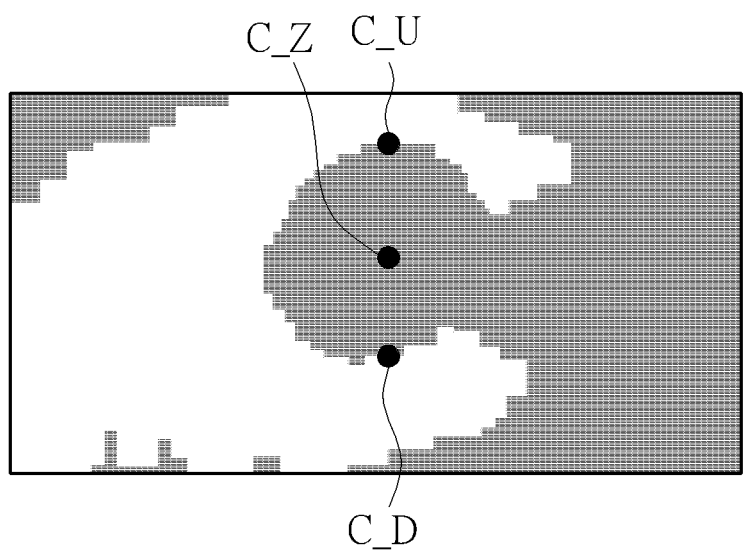
FIG. 7A and FIG. 7B are schematic diagrams of the filling process performed on the binarized image of a region of interest according to an embodiment of the present invention.
Figure 7B:
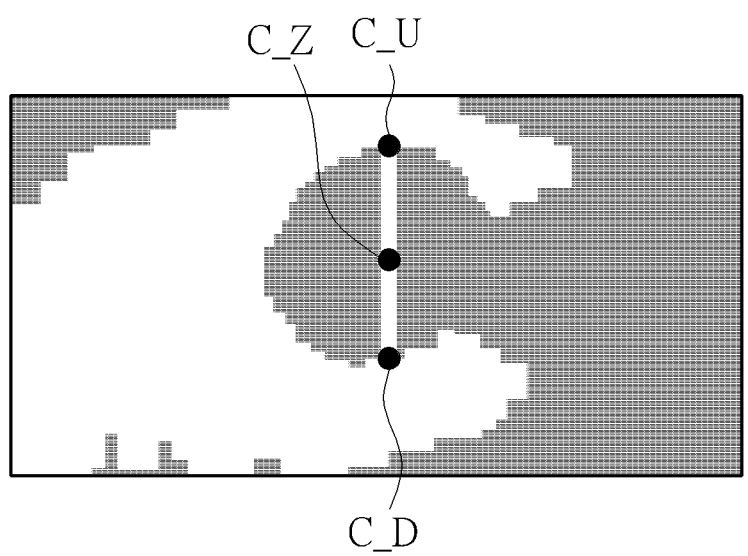

For example, as shown in FIG. 7A, in the binarized image of the region of interest 70, the processor 104 may perform the filling process on the $Z^{th}$ column of pixels. First of all, the processor 104 finds out the middle point C_Z of the $Z^{th}$ column of pixels and determines that the middle point C_Z is in the non-eye region (i.e., the black region) . Subsequently, the processor 104 scans upward from the middle point C_Z. When detecting the eye region (i.e., the white region) at the location of a pixel C_U, the processor 104 may fill the pixel (s) from C_Z to C_U in the $Z^{th}$ column of pixels to be the eye region. The processor 104 then scans downward from the middle point C_Z. When detecting the eye region at the location of a pixel C_D, the processor 104 may fill the pixel(s) from C_Z to C_D in the $Z^{th}$ column of pixels to be the eye region. In addition, the pixel corresponding to the middle point C_Z may also be filled to be the eye region. The image generated after the $Z^{th}$ column of pixels are filled up is illustrated in FIG. 7B.

In other words, the processor 104 may perform the filling process on both the row direction and the column direction in the same manner, to achieve more complete noise filling effects and also solve the problem where the filling process along the row direction cannot fill the noise in the eye corner. In addition, those skilled in the art may also deduce the filling method applied to the condition where the middle point of a column of pixels is in the eye region according to illustrations of FIG. 6A and FIG. 6B; this will not be narrated herein.

Similarly, for the filling along the column direction, the processor 104 may perform the filling process on each column of pixels in the region of interest in order. Alternatively, the processor 104 may selectively perform the filling process on partial columns of pixels in the region of interest according to determination requirements of the degree of eye opening and closure and possible statuses of the eye image, in order to increase the efficiency of performing the filling process and also prevent a waste of operating resources of the processor 104.

The user of the eye detection system 10 may perform the filling process along the row direction or the column direction according to the above illustrations. A more complete filling method is performing the filling process on each row and each column. In several conditions where there are fewer noises or the noise pattern is simple, the filling process may be performed only on partial rows and/or partial columns in order to save resources and increase efficiency. Alternatively, the user may perform the filling process only along the row direction or only along the column direction. Those skilled in the art can arbitrarily adjust the implementation of the filling process according to the above illustrations; this is not limited herein.

After the filling process is accomplished, the eye region in the region of interest may correspond to the eye image of the testee. At this moment, the processor 104 may start to perform determinations of the degree of eye opening and closure. The processor 104 may predefine a detection area and detect the eye size in the detection area, in order to determine the degree of eye opening and closure. Please note that the present invention may determine the degree of eye opening and closure within the detection area formed by multiple columns of pixels, rather than determine the degree of eye opening and closure with the magnitude of the eye region based on only one column of pixels. This prevents wrong determination due to uncompleted filling in the only one column of pixels.

Figure 8:
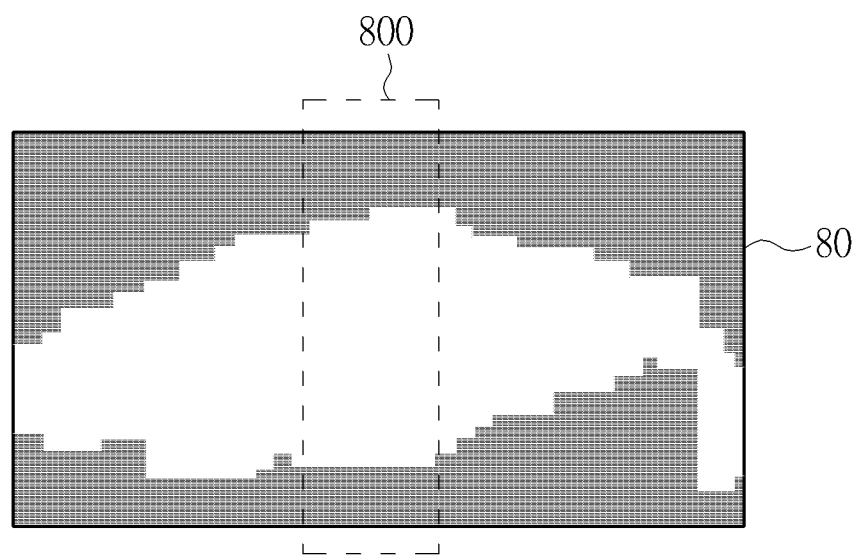
FIG. 8 is a schematic diagram of setting a detection area in the binarized image of a region of interest according to an embodiment of the present invention.

In detail, please refer to FIG. 8, which is a schematic diagram of setting a detection area 800 in the binarized image of a region of interest 80 according to an embodiment of the present invention. As shown in FIG. 8, noise filling has already been performed in the binarized image of the region of interest 80; hence, the region of interest 80 can be utilized for determining the degree of eye opening and closure. The processor 104 may set a detection area in the central region of the region of interest 80 and determine the degree of eye opening and closure according to a distribution of the eye region and the non-eye region within the detection area. The magnitude of the detection area may be arbitrarily determined according to determination requirements. Preferably, if the binarized image is filled along the column direction, the detection area may be set within the range of pixels which undergo the filling process. In other words, the number of columns undergoing the filling process should be greater than or equal to the number of columns within the detection area, so that the noises in the detection area can be effectively filtered.

In addition, in order to prevent eye blinking of the testee from affecting the determination results of the degree of eye opening and closure, the processor 104 may determine the degree of eye opening and closure of the testee's eye according to the determination results on multiple time points during a period of time. For example, the processor 104 may determine that the testee's eye is closed when detecting that the number of times the eye region is smaller than a threshold value reaches a specific number during a specific period of time.

Figure 9:
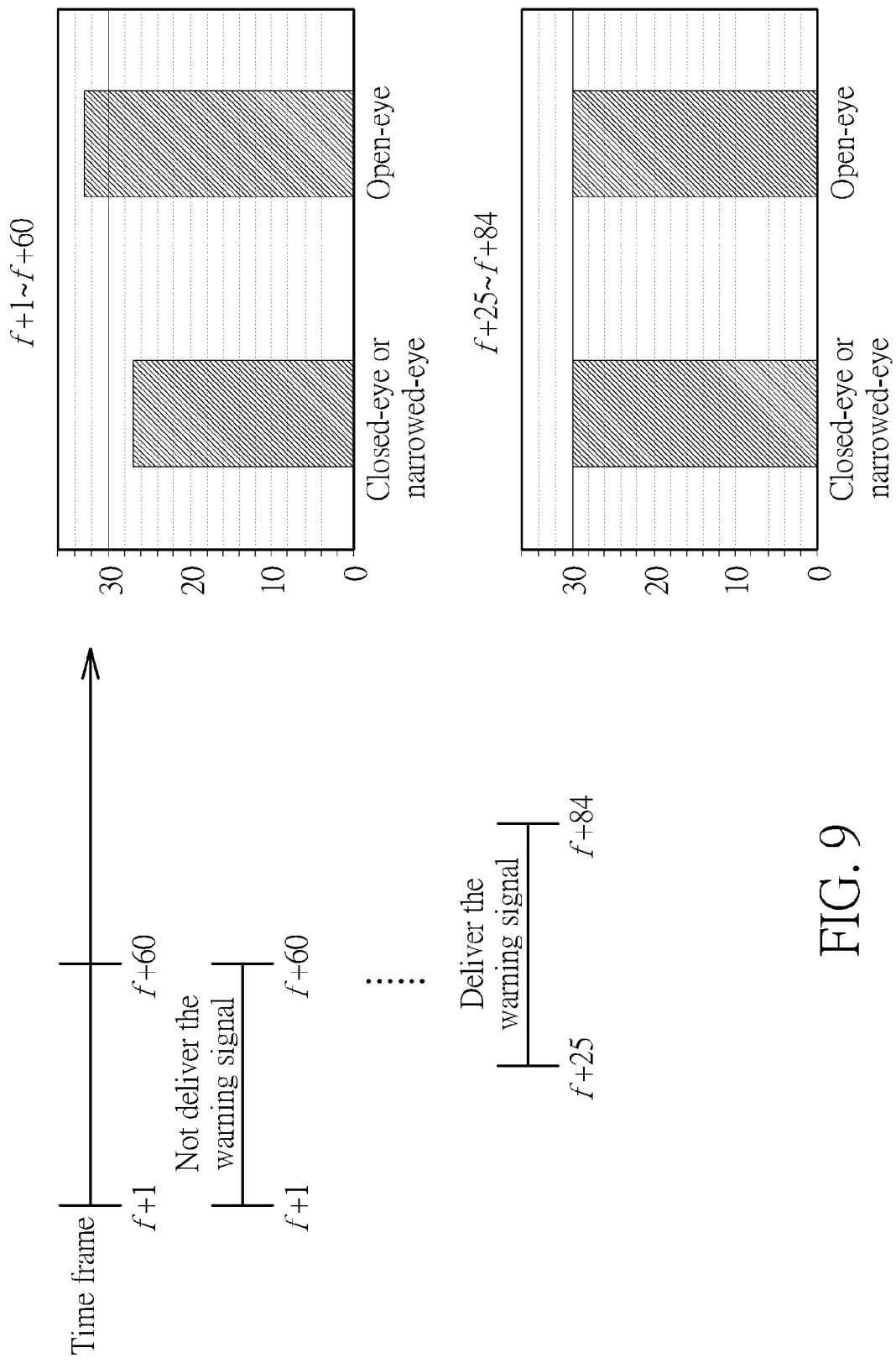
FIG. 9 is a schematic diagram of drowsy detection operations according to an embodiment of the present invention.

For example, please refer to FIG. 9, which is a schematic diagram of drowsy detection operations according to an embodiment of the present invention. As shown in FIG. 9, the processor 104 may configure that a period of time includes 60 time frames, each of which corresponds to one determination result of distributions of the eye region and the non-eye region within the detection area. The determination result may be defined as follows: determining that the testee's eye is open when the ratio of the eye region occupying the detection area is greater than 60%; determining that the testee's eye is narrowed when the ratio of the eye region occupying the detection area is between 40% and 60%; and determining that the testee's eye is closed when the ratio of the eye region occupying the detection area is smaller than 40%. Note that the defined threshold of ratio should not be limited herein, and may be predefined based on the ratio of a testee's eye region occupying the detection area when the testee normally open the eyes, in order to prevent abnormal warning.

In each time frame, the processor 104 may determine whether the testee is sleepy according to the determination results obtained in the time frame and previous 60 time frames. For example, at a time frame f+60, the processor 104 may determine whether the testee is sleepy according to 60 determination results obtained from time frames f+1 to f+60. In such a situation, the processor 104 may be configured to determine that the testee is sleepy when there are more than 30 determination results revealing that the testee's eye is narrowed or closed (i.e., the ratio of the eye region occupying the detection area is smaller than 60%) among every 60 determination results. As shown in FIG. 9, between the time frames f+1 and f+60, there are 27 determination results revealing that the eye is narrowed or closed, and 33 determination results revealing that the eye is open. At this moment, the processor 104 determines that the testee is not drowsy; hence, the warning device 106 will not send a warning signal. At a time frame f+84, the processor 104 obtains that 30 determination results reveals the eye is narrowed or closed and 30 determination results reveals the eye is open according to 60 determination results obtained between the time frames f+25 and f+84. In such a situation, the processor 104 determines that the testee enters a drowsy status and instructs the warning device 106 to deliver a warning signal.

The warning device 106 may be any type of device and may deliver the warning signal by any method. For example, the warning signal may be delivered by a sound; hence, the warning device 106 may include any type of acoustic device in the eye detection system 10. In addition, the warning device 106 may be a light signal in the eye detection system 10, and the light signal is lightened to deliver the warning signal when the testee is determined to be sleepy. In another embodiment, the warning device 106 may be a display device of the eye detection system 10, and the warning signal is displayed on the display device. When the eye detection system 10 is included in a vehicle safety system, the warning device 106 may be realized in the vehicle safety system. The abovementioned types of warning device 106 and various warning signal delivering methods may coexist in the eye detection system 10. The user of the eye detection system 10 may select a proper warning device 106 and the related warning signal delivering method according to requirements, to achieve effective drowsy warning.

Please note that, due to different angles of the photography device 102 taking pictures and different eye sizes of persons, A high probability of wrong determination still exists if a fixed region of interest and a fixed threshold value are utilize for detecting the degree of eye opening and closure. In such a situation, the processor 104 may adjust the magnitude of the threshold value according to the magnitude of the eye region detected within a period of time. For example, in the above embodiments, the threshold for determining whether the testee's eye is open, narrowed or closed in each time frame may be different, and may be adjusted any time based on the detected data of the eye region.

Figure 10:
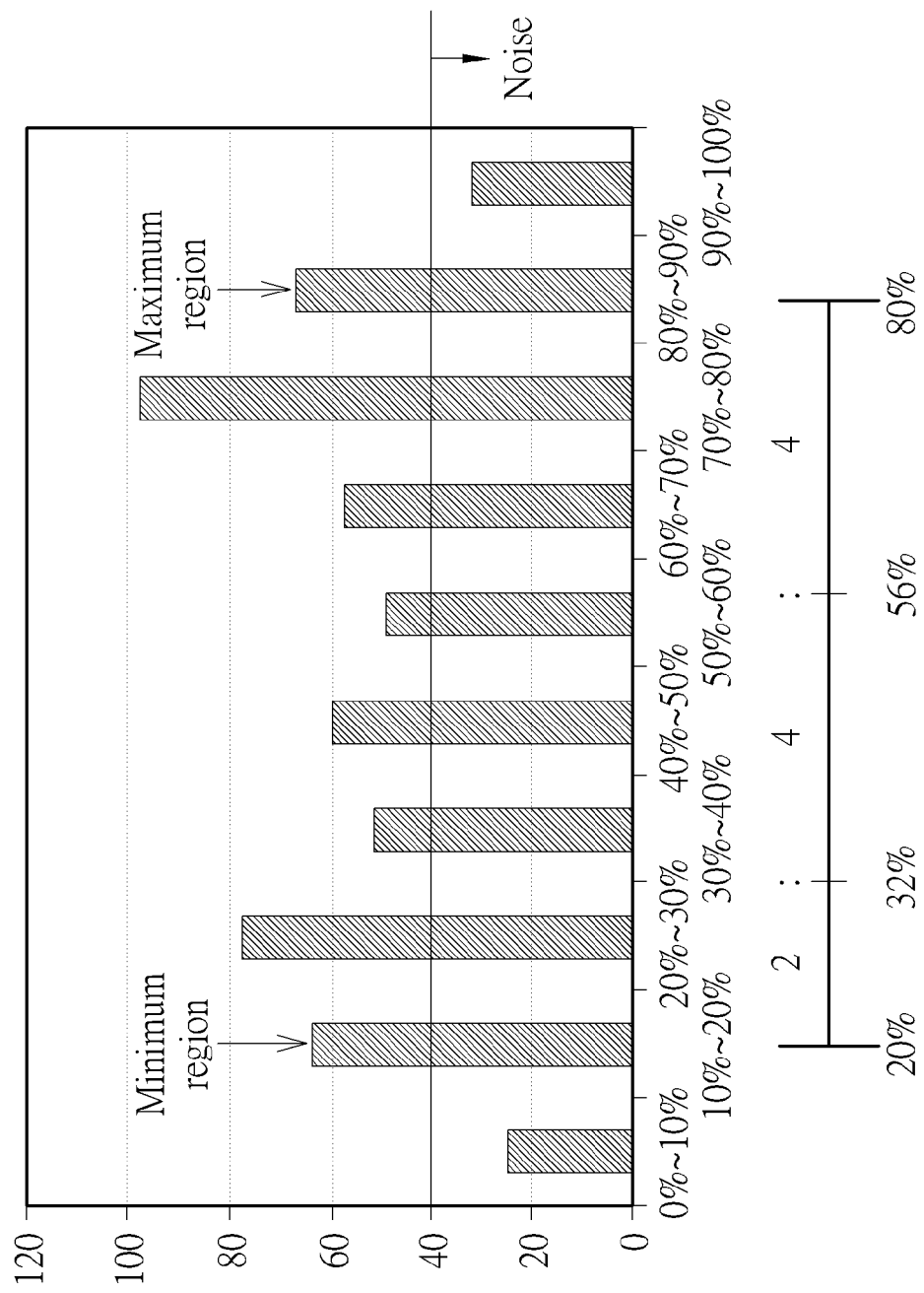
FIG. 10 is a statistical chart of the ratio of the eye region occupying the detection area during a period of time according to an embodiment of the present invention.

A method of adjusting the threshold value applied to the embodiments of the present invention is illustrated in FIG. 10, which is a statistical chart of the ratio of the eye region occupying the detection area during a period of time. In FIG. 10, the determination result in each time frame during the period of time is calculated and utilized for adjusting the threshold values in subsequent period(s). First of all, the ratio of the eye region occupying the detection area ranges from 0% to 100%, which may be divided into 10 statistical regions, wherein a higher ratio represents that the testee's eye tends to be open and a lower ratio represents that the testee's eye tends to be closed. When the number of times accumulated in a statistical region is smaller than a threshold value, this statistical result may be caused by a noise. For example, in FIG. 10, the threshold value for noise determination may be configured to 40, and the total numbers in the regions 0%-10% and 90%-100% are smaller than 40 and thus are regarded as noises and inconsiderable. It should be noted that the open-eye status usually falls within only one or several adjacent statistical regions and the closed-eye status also falls within only one or several adjacent statistical regions when the total number is large enough. Therefore, if the accumulated numbers in some statistical regions are too small, these statistical regions may not correspond to the normal open-eye or closed-eye status; instead, the data in these statistical regions may be generated from uncompleted noise filling or abnormal movements of the testee.

Subsequently, among the statistical regions with the accumulated numbers greater than the threshold value, i.e., 40, the maximum region is 80%-90% and the minimum region is 10%-20%. In such a situation, the processor 104 may allocate the thresholds between the open-eye, narrowed-eye and closed-eye statuses based on a specific ratio, e.g., according to the lower limit of the maximum region and the upper limit of the minimum region within the region 20%-80%. In a preferable embodiment, the regions for allocating the open-eye, narrowed-eye and closed-eye statuses may be determined with a ratio of 4:4:2; that is, within the region 20%-80%, a 24% range in the region (56%-80%) is allocated to the open-eye status, a 24% range in the region (32%-56%) is allocated to the narrowed-eye status, and a 12% range in the region (20%-32%) is allocated to the closed-eye status. Finally, the obtained threshold is: the testee's eye is determined to be open when the ratio of the eye region occupying the detection area is greater than 56%; the testee's eye is determined to be narrowed when the ratio of the eye region occupying the detection area is between 32% and 56%; and the testee's eye is determined to be closed when the ratio of the eye region occupying the detection area is smaller than 32%. Therefore, during a specific period of time such as 60 time frames, the processor 104 may determine that the testee is sleepy when detecting that the total number of times the ratio of the eye region occupying the detection area is smaller than 56% (i.e., the testee's eye is narrowed or closed) reaches a specific number such as 30.

Please note that, the threshold value adjustment method illustrated in FIG. 10 is only one of various implementations. For example, the processor 104 may count the determination results in an arbitrary period length and configure an arbitrary number of statistical regions. The threshold values for determining the noises may also be adjusted according to the statistical time length and the values of statistical data. In addition, in the above embodiments, the processor 104 determines the threshold values for the allocated regions according to the lower limit of the maximum region and the upper limit of the minimum region. In another embodiment, a looser standard such as allocated regions with threshold values based on the upper limit of the maximum region (90%) and the lower limit of the minimum region (10%) may be applied. The standard may be determined to be looser or stricter according to the application environment of the products. In a further embodiment, only one threshold value may be applied to determine whether the status of the testee's eye is open or closed where the narrowed-eye status is excluded. On the other hand, the above ratio of 4:4:2 for the allocation of open-eye, narrowed-eye and closed-eye statuses is only a preferable implementation; this should not be a limitation of the present invention.

Figure 11:
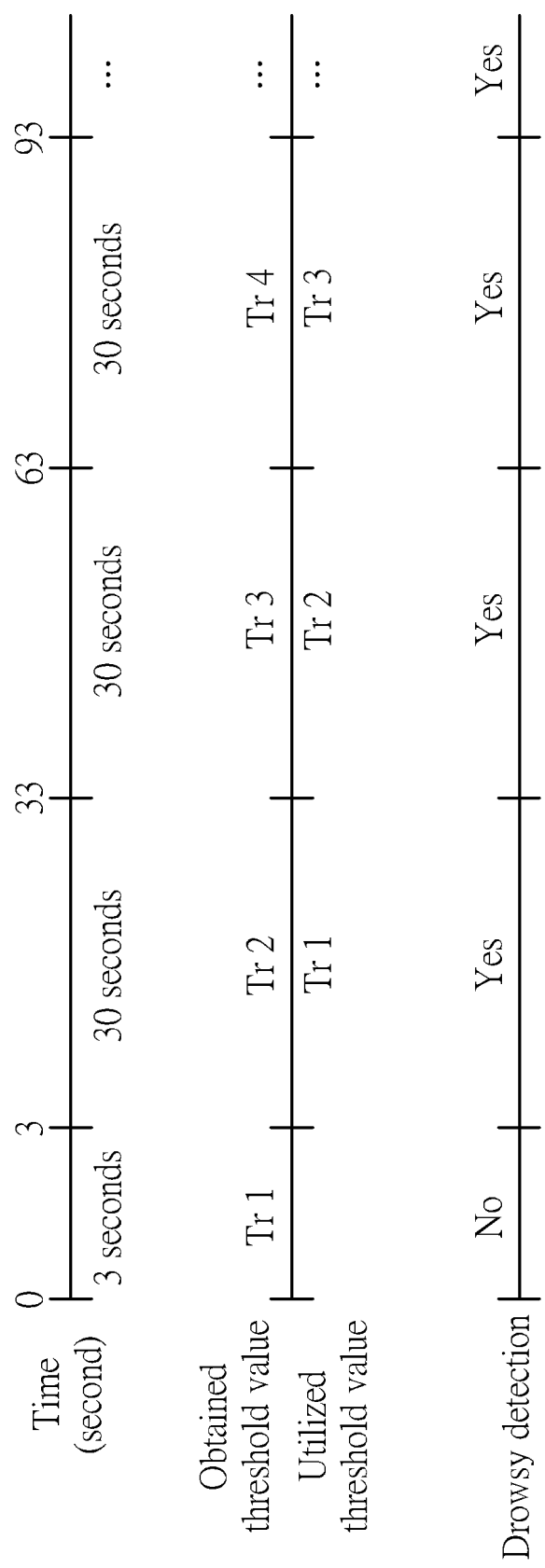
FIG. 11 is a schematic diagram of the operation timing of drowsy detection and threshold adjustment according to an embodiment of the present invention.

Please refer to FIG. 11, which is a schematic diagram of the operation timing of drowsy detection and threshold adjustment (i.e., the thresholds for determining the testee's eye is open, narrowed or closed) according to an embodiment of the present invention. As shown in FIG. 11, when the eye detection system 10 is turned on, a threshold value Tr1 may be determined in the first 3 seconds, and the drowsy detection and determination are not performed in these 3 seconds. In the next 30 seconds (i.e., from the $3^{rd}$ second to the $33^{rd}$ second), the processor 104 may utilize the threshold value Tr1 to perform the drowsy detection and determination. The processor 104 continuously counts the ratio of the eye region occupying the detection area and accordingly generates a threshold value Tr2 in these 30 seconds. In the next 30 seconds (i.e., from the $33^{rd}$ second to the $63^{rd}$ second), the processor 104 then applies the threshold value Tr2 to perform the drowsy detection and determination and also generates a threshold value Tr3 by the abovementioned statistical methods. The operations will keep on by the same token. It should be noted that the operation timing illustrated in FIG. 11 is only one of various implementations. The user of the eye detection system 10 may arbitrarily adjust or determine the time points of changing the threshold values; this is not limited herein.

Figure 12:
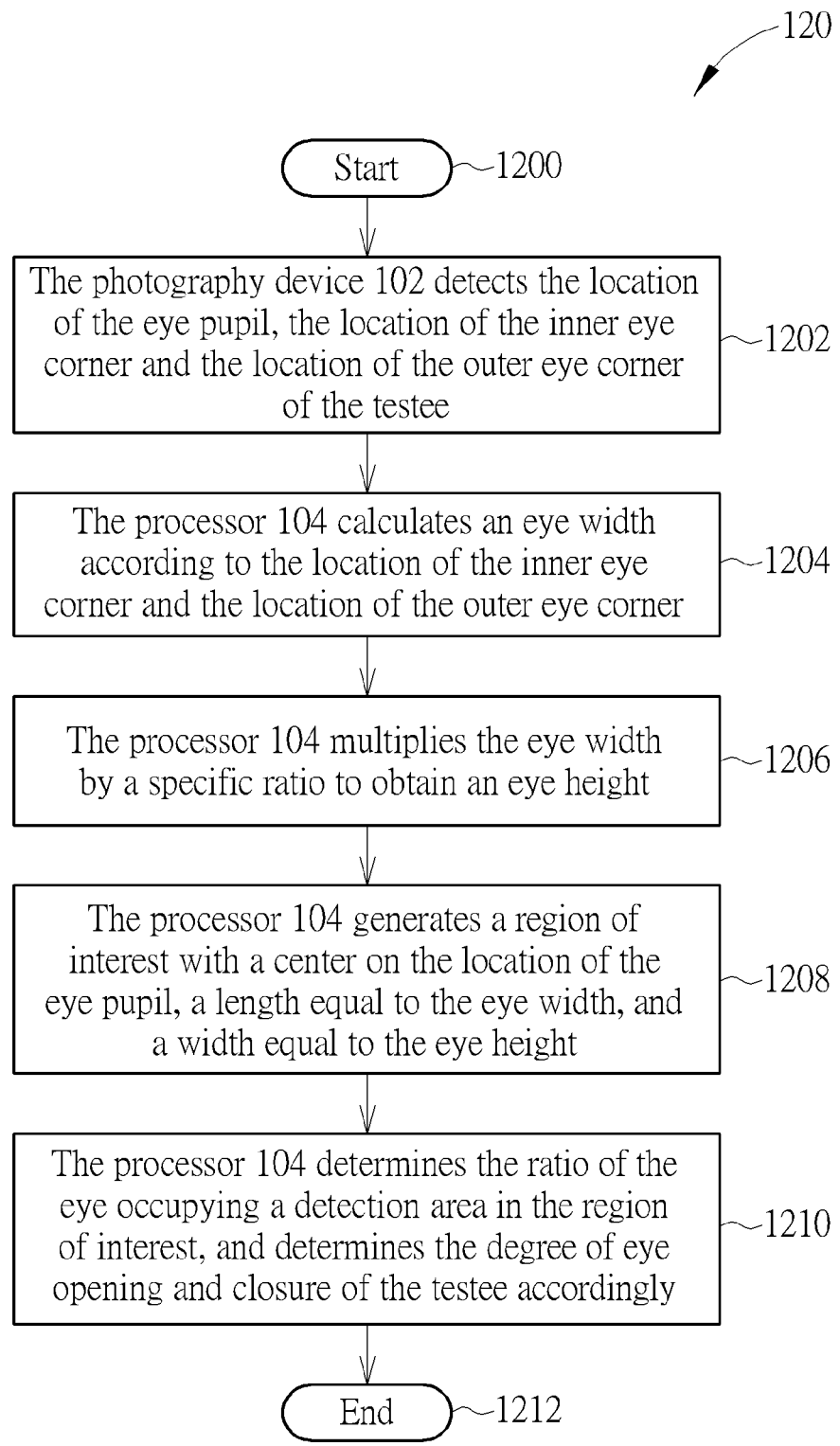
FIG. 12 is a schematic diagram of a drowsy determination process according to an embodiment of the present invention.

The above operations related to the eye detection system 10 may be summarized into a drowsy determination process 120, as shown in FIG. 12. The drowsy determination process 120 includes the following steps:

Step 1200: Start.

Step 1202: The photography device 102 detects the location of the eye pupil, the location of the inner eye corner and the location of the outer eye corner of the testee.

Step 1204: The processor 104 calculates an eye width according to the location of the inner eye corner and the location of the outer eye corner.

Step 1206: The processor 104 multiplies the eye width by a specific ratio to obtain an eye height.

Step 1208: The processor 104 generates a region of interest with a center on the location of the eye pupil, a length equal to the eye width, and a width equal to the eye height.

Step 1210: The processor 104 determines the ratio of the eye occupying a detection area in the region of interest, and determines the degree of eye opening and closure of the testee accordingly.

Step 1212: End.

Figure 13:
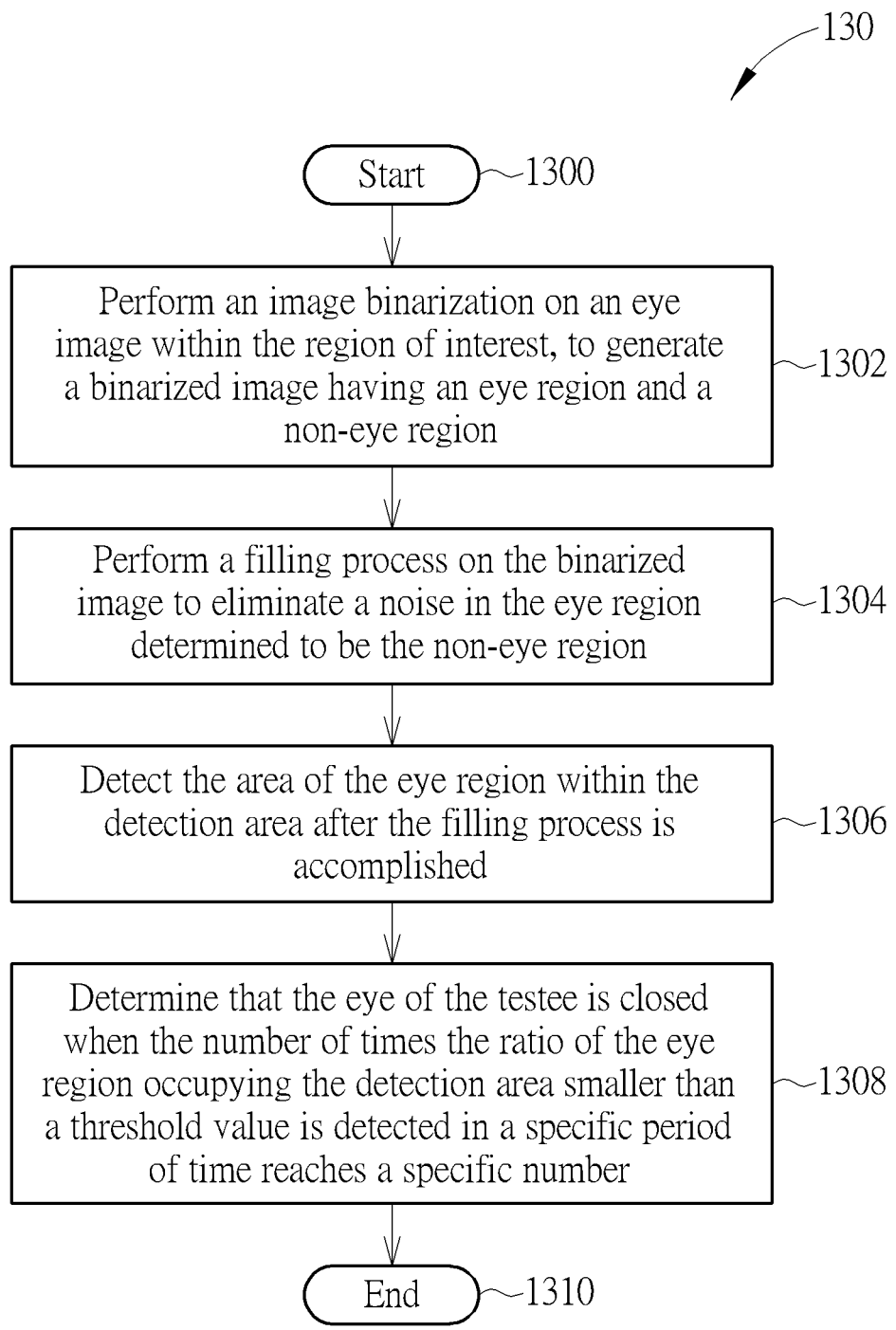
FIG. 13 is a schematic diagram of a determination process according to an embodiment of the present invention.

The above detailed operations related to the processor 104 determining the ratio of the eye region occupying the detection area in the region of interest and accordingly determining the degree of eye opening and closure of the testee may further be summarized into a determination process 130, as shown in FIG. 13. The determination process 130 includes the following steps:

Step 1300: Start.

Step 1302: Perform an image binarization on an eye image within the region of interest, to generate a binarized image having an eye region and a non-eye region.

Step 1304: Perform a filling process on the binarized image to eliminate a noise in the eye region determined to be the non-eye region.

Step 1306: Detect the area of the eye region within the detection area after the filling process is accomplished.

Step 1308: Determine that the eye of the testee is closed when the number of times the ratio of the eye region occupying the detection area smaller than a threshold value is detected in a specific period of time reaches a specific number.

Step 1310: End.

Detailed operations and alternations of the drowsy determination process 120 and the determination process 130 are illustrated in the above paragraphs, and will not be narrated herein.

In the prior art, the drowsy detection systems find out the distance between the upper and lower eyelids to calculate the degree of eye opening and closure, in order to determine whether the driver is sleepy. This method always suffers from positioning difficulty due to eye blinking of the driver. Different eye sizes of different drivers may also result in wrong determination. In contrast, the present invention may determine the region of interest of the eye via the locations of the eye corners, and then determine the degree of eye opening and closure according to the above region of interest. Since the locations of eye corners are fixed and are not easily affected by blinking of eyelids, the present invention is capable of determining whether the testee is sleepy more accurately.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An eye detection method for detecting a degree of eye opening and closure of a testee, comprising:
   detecting a location of an eye pupil, a location of an inner eye corner and a location of an outer eye corner of an eye of the testee;
   calculating an eye width according to the location of the inner eye corner and the location of the outer eye corner;
   multiplying the eye width by a specific ratio smaller than 1 to obtain an eye height;
   generating a rectangular region of interest with a center on the location of the eye pupil, a length equal to the eye width, and a width equal to the eye height; and
   determining a ratio of the eye occupying a detection area in the region of interest, and determining the degree of eye opening and closure of the testee accordingly;
   wherein the step of determining the ratio of the eye occupying the detection area in the region of interest and determining the degree of eye opening and closure of the testee accordingly comprises:
      performing an image binarization on an eye image within the region of interest, to generate a binarized image having an eye region and a non-eye region;
      performing a filling process on the binarized image to eliminate a noise in the eye region determined to be the non-eye region;
      detecting an area of the eye region within the detection area after the filling process is accomplished; and
      determining that the eye of the testee is closed when a number of times the ratio of the eye region occupying the detection area smaller than a threshold value is detected in a specific period of time reaches a specific number.

2. The eye detection method of claim 1, further comprising:
   sending a warning signal when the testee is determined to be sleepy according to the degree of eye opening and closure of the testee.

3. The eye detection method of claim 1, further comprising:
   performing supplementary illumination on the eye, to prevent an image of the eye from being influenced by an external light source.

4. The eye detection method of claim 1, wherein the step of calculating the eye width according to the location of the inner eye corner and the location of the outer eye corner comprises:
   setting the eye width to be equal to a distance between the location of the inner eye corner and the location of the outer eye corner.

5. The eye detection method of claim 1, wherein the filling process comprises:
   determining whether a middle point of a row of pixels in the region of interest is in the eye region or the non-eye region;
   scanning from a first middle point of a first row of pixels toward a direction of the eye width when the first middle point is in the non-eye region, and after scanning to the eye region, filling the non-eye region between the first middle point and the scanned eye region in the first row of pixels to be the eye region; and scanning from a second middle point of a second row of pixels toward the direction of the eye width when the second middle point is in the eye region, and after scanning to the non-eye region and then scanning to the eye region, filling the scanned non-eye region in the second row of pixels to be the eye region.

6. The eye detection method of claim 5, further comprising:
performing the filling process on each row of pixels in the region of interest in order.

7. The eye detection method of claim 1, wherein the filling process comprises:
determining whether a middle point of a column of pixels in the region of interest is in the eye region or the non-eye region;
scanning from a first middle point of a first column of pixels toward a direction of the eye height when the first middle point is in the non-eye region, and after scanning to the eye region, filling the non-eye region between the first middle point and the scanned eye region in the first column of pixels to be the eye region; and
scanning from a second middle point of a second column of pixels toward the direction of the eye height when the second middle point is in the eye region, and after scanning to the non-eye region and then scanning to the eye region, filling the scanned non-eye region in the second column of pixels to be the eye region.

8. The eye detection method of claim 1, further comprising:
adjusting the threshold value according to a magnitude of the eye region detected during a period of time.

9. An eye detection system for detecting a degree of eye opening and closure of a testee, comprising:
a photography device, for detecting a location of an eye pupil, a location of an inner eye corner and a location of an outer eye corner of an eye of the testee; and
a processor, coupled to the photography device, for performing the following steps:
calculating an eye width according to the location of the inner eye corner and the location of the outer eye corner;
multiplying the eye width by a specific ratio smaller than 1 to obtain an eye height;
generating a rectangular region of interest with a center on the location of the eye pupil, a length equal to the eye width, and a width equal to the eye height; and
determining a ratio of the eye occupying a detection area in the region of interest, and determining the degree of eye opening and closure of the testee accordingly;
wherein the processor further performs the following steps to determine the ratio of the eye occupying the detection area in the region of interest and determine the degree of eye opening and closure of the testee accordingly:
performing an image binarization on an eye image within the region of interest, to generate a binarized image having an eye region and a non-eye region;
performing a filling process on the binarized image to eliminate a noise in the eye region determined to be the non-eye region;
detecting an area of the eye region within the detection area after the filling process is accomplished; and
determining that the eye of the testee is closed when a number of times the ratio of the eye region occupying the detection area smaller than a threshold value is detected in a specific period reaches a specific number.

10. The eye detection system of claim 9, further comprising:
a warning device, coupled to the processor, for sending a warning signal when the testee is determined to be sleepy according to the degree of eye opening and closure of the testee.

11. The eye detection system of claim 9, further comprising:
an infrared ray emitter, coupled to the processor, for performing supplementary illumination on the eye, to prevent an image of the eye from being influenced by an external light source.

12. The eye detection system of claim 9, wherein the processor sets the eye width to be equal to a distance between the location of the inner eye corner and the location of the outer eye corner.

13. The eye detection system of claim 9, wherein the filling process comprises:
determining whether a middle point of a row of pixels in the region of interest is in the eye region or the non-eye region;
scanning from a first middle point of a first row of pixels toward a direction of the eye width when the first middle point is in the non-eye region, and after scanning to the eye region, filling the non-eye region between the first middle point and the scanned eye region in the first row of pixels to be the eye region; and
scanning from a second middle point of a second row of pixels toward the direction of the eye width when the second middle point is in the eye region, and after scanning to the non-eye region and then scanning to the eye region, filling the scanned non-eye region in the second row of pixels to be the eye region.

14. The eye detection system of claim 13, wherein the processor performs the filling process on each row of pixels in the region of interest in order.

15. The eye detection system of claim 9, wherein the filling process comprising:
determining whether a middle point of a column of pixels in the region of interest is in the eye region or the non-eye region;
scanning from a first middle point of a first column of pixels toward a direction of the eye height when the first middle point is in the non-eye region, and after scanning to the eye region, filling the non-eye region between the first middle point and the scanned eye region in the first column of pixels to be the eye region; and
scanning from a second middle point of a second column of pixels toward the direction of the eye height when the second middle point is in the eye region, and after scanning to the non-eye region and then scanning to the eye region, filling the scanned non-eye region in the second column of pixels to be the eye region.

16. The eye detection system of claim 9, wherein the processor further adjusts the threshold value according to a magnitude of the eye region detected during a period of time.

17. An eye detection method for detecting a degree of eye opening and closure of a testee, comprising:
performing an image binarization on an eye image within a region of interest, to generate a binarized image having an eye region and a non-eye region;

performing a filling process on the binarized image to eliminate a noise in the eye region determined to be the non-eye region;

detecting an area of the eye region within a detection area in the region of interest after the filling process is accomplished; and determining that the eye of the testee is closed when a number of times the ratio of the eye region occupying the detection area smaller than a threshold value is detected in a specific period of time reaches a specific number;

wherein the filling process comprises:
- determining whether a middle point of a row of pixels in the region of interest is in the eye region or the non-eye region;
- scanning from a first middle point of a first row of pixels toward a direction of the eye width when the first middle point is in the non-eye region, and after scanning to the eye region, filling the non-eye region between the first middle point and the scanned eye region in the first row of pixels to be the eye region; and
- scanning from a second middle point of a second row of pixels toward the direction of the eye width when the second middle point is in the eye region, and after scanning to the non-eye region and then scanning to the eye region, filling the scanned non-eye region in the second row of pixels to be the eye region.

* * * * *